(12) United States Patent
Okubayashi et al.

(10) Patent No.: US 8,440,739 B2
(45) Date of Patent: *May 14, 2013

(54) DENTAL COMPOSITION AND COMPOSITE RESIN

(75) Inventors: Masaki Okubayashi, Kurashiki (JP); Koichi Okada, Tokyo (JP); Yusuke Takahata, Kurashiki (JP); Keisuke Ohtsuka, Kitakyushu (JP)

(73) Assignees: Kuraray Noritake Dental Inc., Kurashiki-shi (JP); JGC Catalysts and Chemicals Ltd., Kawasaki-shi (JP)

( * ) Notice: Subject to any disclaimer, the term of this patent is extended or adjusted under 35 U.S.C. 154(b) by 198 days.

This patent is subject to a terminal disclaimer.

(21) Appl. No.: 12/989,996

(22) PCT Filed: Apr. 28, 2009

(86) PCT No.: PCT/JP2009/058415
§ 371 (c)(1),
(2), (4) Date: Oct. 28, 2010

(87) PCT Pub. No.: WO2009/133911
PCT Pub. Date: Nov. 5, 2009

(65) Prior Publication Data
US 2011/0065828 A1 Mar. 17, 2011

(30) Foreign Application Priority Data

Apr. 28, 2008 (JP) ................................. 2008-117798

(51) Int. Cl.
*A61K 6/083* (2006.01)
*A61K 6/08* (2006.01)
*A61L 24/02* (2006.01)

(52) U.S. Cl.
USPC .......... 523/115; 523/113; 433/228.1; 106/35; 977/919

(58) Field of Classification Search ................. 523/115, 523/113; 433/228.1; 106/35; 977/919
See application file for complete search history.

(56) References Cited

U.S. PATENT DOCUMENTS

| 4,719,297 | A | 1/1988 | Henne et al. |
| 5,055,497 | A | 10/1991 | Okada et al. |

(Continued)

FOREIGN PATENT DOCUMENTS

| EP | 0 009 348 | 4/1980 |
| JP | 57 197289 | 12/1982 |

(Continued)

OTHER PUBLICATIONS

English machine translation of JP 2006052128 A; Aug. 9, 2012.*

(Continued)

*Primary Examiner* — Michael Pepitone
(74) *Attorney, Agent, or Firm* — Oblon, Spivak, McClelland, Maier & Neustadt, L.L.P.

(57) ABSTRACT

A dental composition of the present invention includes: a polymerizable monomer (A); an amorphous filler (B) having an average particle size of 1 to 20 μm and including silica-based fine particles and coatings of an oxide that cover the surfaces of the silica-based fine particles; and inorganic particles (C) having an average particle size of 0.1 to 1.0 μm. The oxide contains a zirconium atom, a silicon atom, and an oxygen atom. It is preferable that the dental composition contain 50 to 400 parts by weight of the filler (B) and 100 to 400 parts by weight of the inorganic particles (C) per 100 parts by weight of the polymerizable monomer (A).

19 Claims, 1 Drawing Sheet

U.S. PATENT DOCUMENTS

| | | | |
|---|---|---|---|
| 5,192,815 A | 3/1993 | Okada et al. | |
| 5,795,497 A | 8/1998 | Kimura et al. | |
| 6,849,112 B2 | 2/2005 | Nishida et al. | |
| 6,849,670 B2 | 2/2005 | Satoh et al. | |
| 6,933,327 B2 * | 8/2005 | Yamakawa et al. | 523/115 |
| 7,981,513 B2 * | 7/2011 | Ohtsuka et al. | 428/403 |
| 2002/0022677 A1 | 2/2002 | Teramae et al. | |
| 2003/0089276 A1 | 5/2003 | Nishida et al. | |
| 2004/0151691 A1 | 8/2004 | Oxman et al. | |
| 2005/0113480 A1 | 5/2005 | Usuki et al. | |
| 2009/0253825 A1 | 10/2009 | Ohtsuka et al. | |
| 2010/0056664 A1 | 3/2010 | Ohtsuka et al. | |

FOREIGN PATENT DOCUMENTS

| | | | |
|---|---|---|---|
| JP | 62-86003 A | 4/1987 | |
| JP | 63 88110 | 4/1988 | |
| JP | 2 28204 | 1/1990 | |
| JP | 2 134307 | 5/1990 | |
| JP | 6 107516 | 4/1994 | |
| JP | 9 169613 | 6/1997 | |
| JP | 9 255516 | 9/1997 | |
| JP | 10 1473 | 1/1998 | |
| JP | 11 92461 | 4/1999 | |
| JP | 2000 159621 | 6/2000 | |
| JP | 2001 139411 | 5/2001 | |
| JP | 2001 302429 | 10/2001 | |
| JP | 2002 138008 | 5/2002 | |
| JP | 2002 204803 | 7/2002 | |
| JP | 3421072 | 4/2003 | |
| JP | 2003 146822 | 5/2003 | |
| JP | 2005 154312 | 6/2005 | |
| JP | 2006 52128 | 2/2006 | |
| JP | 2006052128 A * | 2/2006 | |
| JP | 2006 516544 | 7/2006 | |
| JP | 2007 261967 | 10/2007 | |
| JP | 2008 115136 | 5/2008 | |
| WO | 02 05752 | 1/2002 | |
| WO | 2007 111066 | 10/2007 | |
| WO | 2008 056485 | 5/2008 | |
| WO | WO 2008056485 A1 * | 5/2008 | |

OTHER PUBLICATIONS

U.S. Appl. No. 12/990,077, filed Oct. 28, 2010, Kuboe, et al.
U.S. Appl. No. 12/989,962, filed Oct. 28, 2010, Okubayashi, et al.
International Search Report issued Jul. 28, 2009 in PCT/JP09/58415 filed Apr. 28, 2009.
International Search Report issued Jun. 9, 2009 in PCT/JP09/58417 filed Apr. 28, 2009.
International Search Report issued Jul. 28, 2009 in PCT/JP09/58416 filed Apr. 28, 2009.

* cited by examiner

DENTAL COMPOSITION AND COMPOSITE RESIN

CROSS-REFERENCE TO RELATED APPLICATIONS

This application is a 371 of PCT/JP2009/058415 filed Apr. 28, 2009. Priority to Japan 2008-117798, filed Apr. 28, 2008, is claimed.

TECHNICAL FIELD

The present invention relates to a dental composition that can be used suitably as a dental material, particularly a dental composite resin, that can be used as a substitute for a part of a natural tooth or an entire natural tooth in the field of dental treatment.

BACKGROUND ART

A dental composition containing a polymerizable monomer, a filler, and a polymerization initiator is called a composite resin, and this dental composition is most widely used today as a restorative material for repairing fractures of teeth and dental caries. Such a dental composition is required to have the following properties. Specifically, as a cured product obtained after polymerization curing, the dental composition is required to have sufficient mechanical strength and hardness to serve as a substitute for natural teeth, wear resistance against occlusion of teeth in an oral cavity, surface smoothness and gloss, color matching with natural teeth, transparency, etc. Furthermore, as a paste which has not yet been polymerized and cured, the dental composition is desired to have ease of handling (high handling properties) for dental clinicians and technicians, for example, proper fluidity and forming property, no adhesion to dental instruments, no stickiness, etc.

These properties of the dental composition are greatly influenced by the component materials, shape, particle size, and content of fillers used therein and by the combination of the fillers used together. For example, when an inorganic filler having an average particle size of more than 1 μm is used, the filling rate of the filler in the polymerizable monomer can be increased easily and therefore sufficient mechanical strength as a cured product and high handling properties as a paste can be obtained. The use of such an inorganic filler has, however, a drawback in that it is difficult to obtain satisfactory gloss even after final polishing, and even if satisfactory gloss is obtained, the gloss cannot be retained for a long time. On the other hand, when an inorganic ultrafine particle filler having an average particle size of 1 μm or less is used, the surface smoothness and gloss after polishing of the cured product and the gloss durability in the oral cavity are improved. The use of such an inorganic ultrafine particle filler has, however, a drawback in that when the inorganic filler is mixed and kneaded with the polymerizable monomer, the viscosity of the resulting paste increases significantly, which makes it difficult to increase the content of the filler. As a result, the mechanical strength of the cured product decreases, and the unpolymerized pasty composition becomes sticky, which reduces the handling properties. Furthermore, when an organic-inorganic composite filler obtained by mixing inorganic ultrafine particles having an average particle size of 100 nm or less with a polymerizable monomer, curing the mixture, and grinding the resulting cured product is used, the handling properties of the paste are improved, but the content of the inorganic filler in the cured product still is insufficient. Since the surface of the organic-inorganic composite filler forms a weak bond with the matrix, the mechanical strength of the cured product is not sufficient. Under these circumstances, it is difficult to increase the mechanical strength and the surface smoothness and gloss after polishing of the cured product and the handling properties of the paste in a balanced manner.

In recent development of dental compositions, various methods have been proposed to solve conventional problems such as the stickiness of pastes and insufficient mechanical strength while inorganic ultrafine particles are used as a main component to ensure the surface smoothness and gloss after polishing. For example, Patent Literature 1 listed below describes a dental composite resin containing an organic-inorganic composite filler having an average particle size of 1 to 30 μm and a glass powder having a particle size range of 0.1 to 100 μm and an average particle size of 0.2 to 20 μm. The organic-inorganic composite filler is obtained by mixing ultrafine particle silica having an average particle size of 0.01 to 0.05 μm with a polymerizable monomer, polymerizing and curing the mixture, and grinding the resulting cured product.

Patent Literature 2 discloses a technique of using, as a filler, an aggregate having a primary particle size of 1 to 250 nm and obtained by heat treatment of silica and at least one metal oxide other than silica. For example, Patent Literature 2 discloses a dental composition using, as a filler, an aggregate of silica-based fine particles and zirconia fine particles, obtained by mixing a silica sol having an average particle size of 15 nm and a zirconia sol having an average particle size of 23 nm, and subjecting the mixture to spray drying and heat treatment.

Citation List
Patent Literature
  Patent Literature 1 JP 63 (1988)-88110 A
  Patent Literature 2 JP 2001-302429 A

SUMMARY OF INVENTION

Technical Problem

In the dental composite resin described in Patent Literature 1, the use of the organic-inorganic composite filler having a large particle size improves the problems of a significant increase in the viscosity and stickiness of the paste, and the addition of the glass powder enhances the mechanical strength of the cured product. This dental composite resin, however, has the following drawbacks: the substantial content of the inorganic filler cannot be increased sufficiently; the surface of the organic-inorganic composite filler and the polymerizable monomer used in combination with this filler cannot be connected substantially by a chemical bond, and therefore the bond between the filler and the polymerizable monomer at the interface therebetween is weak; and the glass powder has a large average particle size of 4 to 5 μm, and therefore it is difficult to obtain satisfactory surface smoothness and gloss after polishing and gloss durability. Therefore, there is room for improvement.

The dental composition described in Patent Literature 2 uses, as a filler, aggregated particles having a large particle size in their appearance. These aggregated particles are obtained by aggregating silica fine particles together with fine particles of a metal oxide, such as zirconium oxide, and so on to have a larger particle having a micron-size or more. Therefore, the properties of the paste are improved, and the mechanical strength of the cured product also is enhanced. However, since the aggregation strength between respective fine particles is weak, the mechanical strength of the dental composition is not sufficient for the dental composition.

The present invention has been made in order to solve the above conventional problems, and it is an object of the present invention to provide a dental composition exhibiting both excellent mechanical strength, surface smoothness and gloss after polishing, and gloss durability as a cured product, and good handling properties as a paste. It is another object of the present invention to provide a composite resin both exhibiting excellent mechanical strength, surface smoothness and gloss after polishing, and gloss durability as a cured product, and good handling properties as a paste.

Solution to Problem

The dental composition of the present invention includes: a polymerizable monomer (A); an amorphous filler (B) having an average particle size of 1 to 20 μm and including silica-based fine particles and coatings of an oxide that cover the surfaces of the silica-based fine particles; and inorganic particles (C) having an average particle size of 0.1 to 1.0 μm. The oxide contains a zirconium atom, a silicon atom, and an oxygen atom.

The present invention also provides a composite resin using the above dental composition of the present invention.

Advantageous Effects of Invention

According to the dental composition of the present invention, a cured product having high mechanical strength can be obtained. In addition, the cured product also has high surface smoothness and gloss after polishing and high gloss durability, and therefore, the dental composition of the present invention has a good aesthetic appearance. Furthermore, the dental composition of the present invention has, as a paste, good handling properties and proper fluidity and forming property, and the adhesion to dental instruments and stickiness are reduced. That is, this dental composition is very easy to handle. The dental composition of the present invention can be used particularly suitably as a composite resin, and this composite resin has excellent mechanical strength, surface smoothness and gloss after polishing, and gloss durability as a cured product, and good handling properties as a paste.

DESCRIPTION OF EMBODIMENTS

Figure 1:
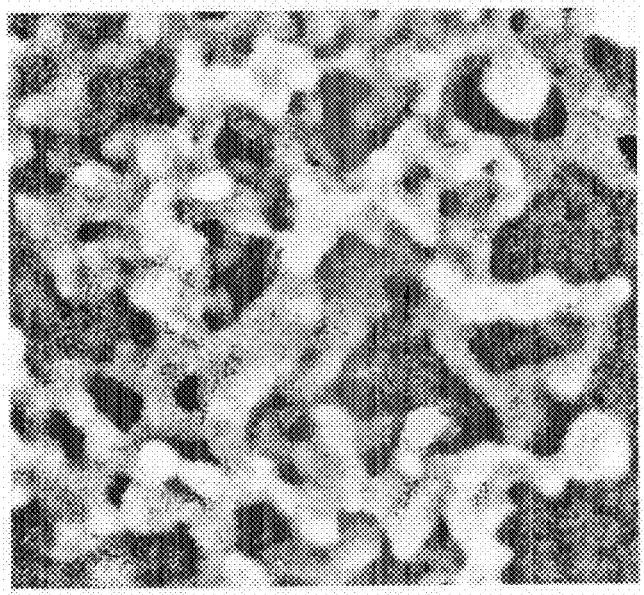
FIG. 1 is an SEM micrograph (×500000) of one example of a filler (B) which has been subjected to a drying process.

As the polymerizable monomer (A) used in the present invention, a known polymerizable monomer used for dental compositions can be used without any limitation. Generally, a radical polymerizable monomer is used suitably. Specific examples of the radical polymerizable monomer in the polymerizable monomer (A) include esters of α-cyanoacrylic acid, (meth)acrylic acid, α-halogenated acrylic acid, crotonic acid, cinnamic acid, sorbic acid, maleic acid, itaconic acid, etc., (meth)acrylamide, (meth)acrylamide derivatives, vinyl esters, vinyl ethers, mono-N-vinyl derivatives, styrene derivatives, and the like. Among them, (meth)acrylic acid esters are preferred. In the present invention, "(meth)acryl" means methacryl or acryl.

Examples of (meth)acrylic acid ester-based polymerizable monomers are given hereinbelow.

(1) Monofunctional (meth)acrylates include:

methyl (meth)acrylate, isobutyl (meth)acrylate, benzyl (meth)acrylate, lauryl (meth)acrylate, 2-(N,N-dimethylamino)ethyl (meth)acrylate, 2,3-dibromopropyl (meth)acrylate, 2-hydroxyethyl (meth)acrylate, 6-hydroxyhexyl (meth)acrylate, 10-hydroxydecyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, N-(dihydroxyethyl) (meth)acrylamide, (meth)acryloyloxydodecylpyridinium bromide, (meth)acryloyloxydodecylpyridinium chloride, (meth)acryloyloxyhexadecylpyridinium chloride, (meth)acryloyloxydecylammonium chloride, and the like.

(2) Bifunctional (meth)acrylates include:

ethylene glycol di(meth)acrylate, triethylene glycol di(meth)acrylate, propylene glycol di(meth)acrylate, neopentyl glycol di(meth)acylate, 1,6-hexanediol di(meth)acrylate, 1,10-decanediol di(meth)acrylate, bisphenol A diglycidyl (meth)acrylate (2,2-bis[4-[3-(meth)acryloyloxy-2-hydroxypropoxy]phenyl]propane, commonly known as "Bis-GMA"), 2,2-bis[4-(meth)acryloyloxyethoxyphenyl]propane, 2,2-bis[4-(meth)acryloyloxypolyethoxyphenyl]propane, 2,2-bis[4-[3-((meth)acryloyloxy-2-hydroxypropoxy]phenyl]propane, 1,2-bis[3-(meth)acryloyloxy-2-hydroxypropoxy]ethane, pentaerythritol di(meth)acrylate, [2,2,4-trimethylhexamethylenebis(2-carbamoyloxyethyl)]dimethacrylate, and the like.

(3) Trifunctional or higher polyfunctional (meth)acrylates include:

trimethylolpropane tri(meth)acrylate, trimethylolethane tri(meth)acrylate, tetramethylolmethane tri(meth)acrylate, pentaerythritol tetra(meth)acrylate, dipentaerythritol hexa(meth)acrylate, N,N'-(2,2,4-trimethylhexamethylene)bis[2-(aminocarbonyloxy)propane-1,3-diol]tetramethacrylate, 1,7-diacryloyloxy-2,2,6,6-tetraacryloyloxymethyl-4-oxyheptane, and the like.

Any one of the above-mentioned polymerizable monomers can be used alone or as a mixture of two or more kinds thereof.

To improve the adhesion to tooth structures, metals, ceramics, and the like, it is preferable in some cases that the polymerizable composition of the present invention contain, as a polymerizable monomer, a functional monomer for providing adhesion to these adherends.

As such functional monomers, for example, monomers having a phosphoric acid group, such as 2-(meth)acryloyloxyethyl dihydrogenphosphate, 10-(meth)acryloyloxydecyl dihydrogenphosphate, and 2-(meth)acryloyloxyethyl phenyl hydrogenphosphate, and monomers having a carboxylic acid group, such as 11-(meth)acryloyloxy-1,1-undecanedicarboxylic acid and 4-(meth)acryloyloxyethoxycarbonyl phthalic acid are preferred because these monomers exhibit excellent adhesion to tooth structures and base metals.

As such functional monomers, for example, 10-mercaptodecyl (meth)acrylate, 6-(4-vinylbenzyl-n-propyl)amino-1,3,5-triazine-2,4-dithione, a thiouracil derivative described in JP 10 (1998)-1473 A, and a sulfur element-containing compound described in JP 11 (1999)-92461 A are preferred because these monomers exhibit excellent adhesion to precious metals.

Furthermore, as such a functional monomer, for example, a silane coupling agent such as γ-methacryloxypropyl trimethoxysilane is effective in bonding to ceramics, porcelains, and dental composite resins.

The filler (B) used for the dental composition of the present invention includes silica-based fine particles and coatings of an oxide that cover the surfaces of the silica-based fine particles. The oxide contains a zirconium atom, a silicon atom, and an oxygen atom.

The silica-based fine particles mean fine particles containing 80 mol % or more of $SiO_2$ in terms of oxides. The components other than $SiO_2$ are not particularly limited as long as they do not impair the advantageous effects of the present invention. Examples of the components include $TiO_2$, $ZrO_2$, $Al_2O_3$, and $Na_2O$. Preferably, the content of $SiO_2$ is 90 mol % or more. It is preferable that the content of $SiO_2$ be substantially 100 mol % (that is, the content be 100% except for unavoidable impurities). Preferably, the average particle size of the silica-based fine particles is 2 to 300 nm. When the average particle size is less than 2 nm, the resulting cured product of the dental composition may have insufficient mechanical strength. When the dental composition containing the silica-based fine particles having an average particle size of more than 300 nm is used to restore teeth, the cured product may have reduced transparency or insufficient surface smoothness and gloss after polishing. The average particle size of the silica-based fine particles can be determined by the dynamic light scattering method. For example, 7.0 g of an aqueous dispersion sol containing silica-based fine particles (having a solid content of 20% by weight) is placed in a cylindrical stainless steel cell with a size of 3 cm length, 2 cm width and 2 cm height equipped with a transmission window, and the particle size distribution is measured using an ultrafine particle size distribution analyzer of dynamic light scattering type (Model 9340-UPA150 manufactured by Honeywell). Thus, the average particle size can be calculated.

In the present invention, an "amorphous" filler (B) means that when the inorganic powder obtained as the filler (B) is subjected to an X-ray diffraction analysis by X-ray diffractometry using an X-ray diffractometer ("RINT-1400" manufactured by Rigaku Corporation) under the following conditions, no diffraction peak is observed.
(Conditions for X-Ray Diffraction Analysis)
2θ: 10-70 degrees
Scan speed: 2 degrees/min
Tube voltage: 30 kV
Tube current: 130 mA The oxide that covers the surface of the silica-based fine particle contains a zirconium atom, a silicon atom, and an oxygen atom. The oxide further may contain a titanium atom, an aluminum atom, etc. This oxide coating on the surface of the silica-based fine particle approximates the refractive index of the filler (B) to that of the polymerizable monomer (A). As a result, the dental composition exhibits excellent transparency, and the cured product of the dental composition has high mechanical strength.

Specific examples of the structure of the oxide are shown below.

[Chemical Formula 1]

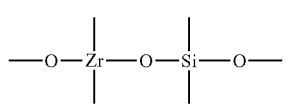

(I)

[Chemical Formula 2]

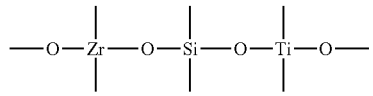

(II)

[Chemical Formula 3]

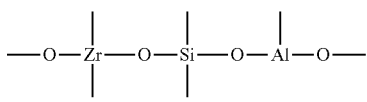

(III)

In the filler (B), the oxide coating may cover each of the silica-based fine particles, or may cover a plurality of silica-based fine particles. In the preferred embodiment, the oxide coating covers a plurality of silica-based fine particles. In this case, the filler (B) has a structure in which the oxide coating of a silica-based fine particle and the oxide coating of a neighboring silica-based fine particle are connected with each other. In this regard, it is preferable that the filler (B) have a structure in which the oxide coating of a silica-based fine particle and the oxide coating of a neighboring silica-based fine particle extend and are connected with each other. In the case where the silica-based fine particles are connected through the oxide coatings in the manner as described above, the silica-based fine particles are bonded to each other more strongly than they are aggregated together by intermolecular force. Accordingly, the use of this filler (B) in the dental material further increases the mechanical strength. Furthermore, as the dental material is abraded, the connecting portion between the oxide coatings is ruptured and thereby only a part of the filler (B) comes off. Therefore, the use of this filler (B) also increases the surface smoothness and gloss after polishing. From the viewpoint of the surface smoothness and gloss after polishing, it is preferable that, in the outer shape of this connection structure, the connecting portion between the oxide coatings be thinner than a portion where the silica-based fine particle is covered by the oxide coating. In other words, it is preferable that the thickness of the connecting portion between the oxide coatings be smaller than the sum of the largest dimension of the silica-based fine particle in the thickness direction and the thicknesses of two portions of the oxide coating of that particle.

Figure 2:
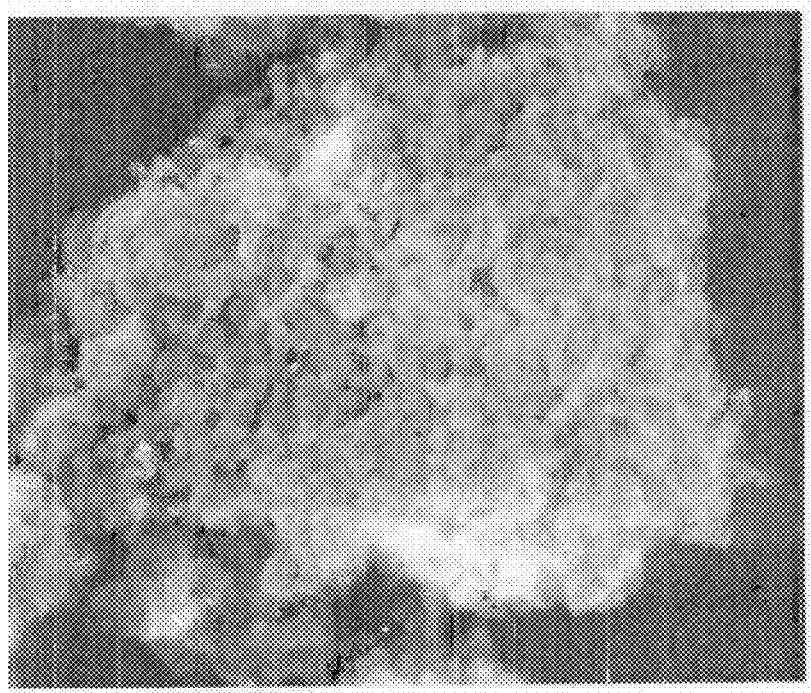
FIG. 2 is an SEM micrograph (×300000) of another example of a filler (B) which has been subjected to a drying process.

It is more preferable, in the structure of the filler (B), that one oxide coating of a silica-based fine particle is connected with a plurality of oxide coatings of neighboring silica-based fine particles. In this case, the filler (B) may have a structure, such as a tetrapod structure, or a star structure, in which a plurality of silica-based fine particles are connected through the oxide coatings to one silica-based fine particle with the one silica-based fine particle being placed in the center of the structure, or may have a branched three-dimensional network structure, in which the plurality of silica-based fine particles connected to one silica-based fine particle through the oxide coatings are connected further with other silica-based fine particles. In this three-dimensional network structure, silica-based fine particles are present at the ends of the branches and the branch points. Silica-based fine particles may be present at positions other than the ends of the branches and the branch points. It is particularly preferable that the filler (B) have a porous particle structure in which the oxide coatings are connected to each other to form an aggregate of the silica-based fine particles covered with the oxide coatings. FIG. 1 and FIG. 2 show SEM micrographs of examples of the filler (B) used in the present invention.

The thickness of the oxide coating may be determined appropriately in consideration of the particle size of the above silica-based fine particles, the thickness of the surface-treated layer to be described later, and the particle size of the filler (B) to be described later.

The filler (B) may further include, if necessary, a surface-treated layer of at least one organic metal compound selected from the group consisting of an organic silicon compound, an organic titanium compound, an organic zirconium compound, and an organic aluminum compound on the oxide coating. With this surface-treated layer, the refractive index of the filler (B) can be adjusted. Furthermore, this surface-treated layer enhances the dispersibility of the filler (B) in the polymerizable monomer (A) and the adhesion between the polymerizable monomer (A) and the filler (B). When two or more different kinds of organic metal compounds are used, the surface-treated layer may be made of a mixture of these two or more different kinds of organic metal compounds, or may have a multilayer structure in which the two or more different organic metal compound layers are laminated.

An example of the organic silicon compound is a compound represented by $R^1{}_nSiX_{4-n}$ (where $R^1$ is a substituted or unsubstituted hydrocarbon group having 1 to 12 carbon atoms, X is an alkoxy group having 1 to 4 carbon atoms, a hydroxyl group, a halogen atom, or a hydrogen atom, and n is an integer of 0 to 3. If a plurality of $R^1$s and a plurality of Xs are present, the $R^1$s may be the same as or different from one another, and the Xs may be the same as or different from one another.)

Specific examples of the organic silicon compound include methyltrimethoxysilane, dimethyldimethoxysilane, phenyltrimethoxysilane, diphenyldimetoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyl-tris(β-methoxyethoxy)silane, 3,3,3-trifluoropropyl trimethoxysilane, methyl-3,3,3-trifluoropropyl dimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropylmethyldiethoxysilane, N-β(aminoethyl)γ-aminopropylmethyldimethoxysilane, N-β(aminoethyl)γ-aminopropyltrimethoxysilane, N-β(aminoethyl)γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyl trimethoxysilane (having 3 to 12 carbon atoms between a (meth)acryloxy group and a silicon atom, for example, γ-methacryloxypropyltrimethoxysilane, or the like), ω-(meth)acryloxyalkyl triethoxysilane (having 3 to 12 carbon atoms between a (meth)acryloxy group and a silicon atom, for example, γ-methacryloxypropyltriethoxysilane, or the like), and the like.

Among them, a coupling agent having a functional group that is copolymerizable with the polymerizable monomer (A), for example, ω-(meth)acryloxyalkyl trimethoxysilane (having 3 to 12 carbon atoms between a (meth)acryloxy group and a silicon atom), ω-(meth)acryloxyalkyl triethoxysilane (having 3 to 12 carbon atoms between a (meth)acryloxy group and a silicon atom), vinyltrimethoxysilane, vinyltriethoxysilane, vinyltriacetoxysilane, γ-glycidoxypropyltrimethoxysilane, or the like is used particularly preferably in the dental composition of the present invention.

Examples of the organic titanium compound include tetramethyl titanate, tetraisopropyl titanate, tetra-n-butyl titanate, butyl titanate dimmer, and tetra(2-ethylhexyl) titanate.

Examples of the organic zirconium compound include zirconium isopropoxide, zirconium-n-butoxide, zirconium acetylacetonate, and zirconyl acetate.

Examples of the organic aluminum compound include aluminum acetylacetonate and a chelate compound of a salt of aluminum and an organic acid.

Furthermore, the filler (B) contained in the dental composition of the present invention contains zirconium, and further may contain metal elements such as aluminum and titanium. Therefore, an organic phosphorus compound disclosed in JP 02(1990)-28204A also is used preferably as a surface treating agent for the filler (B) in some cases.

The method for the surface treatment is not particularly limited, and a commonly known method can be applied thereto. When two or more different kinds of surface treating agents are used, the surface-treated layer may be made of a mixture of these two or more different kinds of organic metal compounds, or may have a multilayer structure in which the two or more different organic metal compound layers are laminated. This surface treatment improves the affinity between the polymerizable monomer (A) and the filler (B), and thereby enhances the dispersibility and adhesion. As a result, the mechanical strength of the cured product can be increased.

The average particle size of the filler (B) is 1 to 20 μm, preferably 2 to 15 μm, and more preferably 3 to 10 μm. When the average particle size is less than 1 μm, the resulting paste becomes sticky, which may cause insufficient handling properties. When the average particle size exceeds 20 μm, the sagging of the paste develops, which may impair the handling properties. If the filler (B) consists of aggregated particles, the above-mentioned average particle size is the average particle size of the aggregated particles.

The average particle size of the filler (B) can be obtained by the laser diffraction/scattering method. More specifically, for example, the average particle size can be obtained by the measurement using a 0.2% aqueous solution of sodium hexametaphosphate as a dispersion medium, with a laser diffraction particle size distribution analyzer (SALD-2100 manufactured by Shimadzu Corporation). As stated herein, the average particle size refers to the volume median particle size, which is a particle size at a cumulative volume frequency of 50% when calculated based on the volume fraction of the particles from the smaller particle size side.

The overall shape of the particles of the filler (B) is not particularly limited. The filler (B) can be used as an irregular-shaped or spherical powder. If the irregular-shaped filler (B) is used, a dental composition having particularly excellent mechanical strength and wear resistance can be obtained, and if the spherical filler (B) is used, a dental composition having particularly excellent surface smoothness and gloss after polishing and gloss durability can be obtained. The shape of the filler (B) may be selected suitably in accordance with the intended use of the dental composition.

The refractive index of the filler (B) is not particularly limited, but if the refractive index of the filler (B) is approximated to that of the polymerizable monomer (A), the transparency of the cured product of the dental composition can be increased easily. Therefore, the refractive index of the filler (B) is preferably 1.45 to 1.65, more preferably 1.50 to 1.60, and particularly preferably 1.52 to 1.58. The refractive index of the filler (B) can be controlled by adjusting the content ratio of the metal elements in the oxide, adjusting the thickness of the above-described oxide coating, forming the above-described surface-treated layer, etc.

The amount of the filler (B) to be added is preferably 50 to 400 parts by weight per 100 parts by weight of the polymerizable monomer (A), more preferably 75 to 350 parts by weight, and particularly preferably 100 to 300 parts by weight. In the dental composition of the present invention, the filler (B) has a structure in which surfaces of silica-based fine particles are covered with coatings of an oxide containing a zirconium atom, a silicon atom, an oxygen atom, etc. Therefore, the content of the filler (B) can be increased while the increase in the viscosity and the stickiness of the paste are prevented. As a result, the mechanical strength can be increased further.

There is no particular limitation on the production method of the filler (B). For example, the filler (B) can be produced by the following steps:

(1) adding a hydroxide of an alkali metal and hydrogen peroxide to an aqueous solution containing a zirconium oxide hydrate and stirring the mixture to prepare a mixed aqueous solution in which the zirconium oxide hydrate is peptized;

(2) adding, under stirring, the mixed aqueous solution obtained in the above step (1) and an aqueous solution of a silicic acid solution to a silica sol in which silica-based fine particles having an average particle size of 2 to 300 nm are dispersed in water;

(3) treating the mixed aqueous solution obtained in the above step (2) with a cation-exchange resin to remove alkali cations;

(4) putting the mixed aqueous solution obtained in the above step (3) into a reaction vessel and subjecting the mixed aqueous solution to a hydrothermal treatment at a temperature of 100 to 350° C. to prepare a mixed aqueous solution containing the filler (B) in which the surfaces of the silica-based fine particles are covered with coatings of an oxide containing at least a zirconium atom, a silicon atom, and an oxygen atom; and (5) drying the filler (B) contained in the mixed aqueous solution obtained in the above step (4).

The zirconium oxide hydrate ($ZrO_2 \cdot xH_2O$) used in the step (1) can be prepared by a conventionally known method, for example, by hydrolyzing a zirconium salt in an aqueous solution, or by adding alkali or ammonia to an aqueous solution of a zirconium salt to cause a neutralization reaction. The zirconium oxide hydrate is obtained, for example, by adding, under stirring, ammonia or aqueous ammonia to an aqueous solution of one or more zirconates selected from zirconium oxychloride, zirconium oxysulfate, zirconium oxynitrate, zirconium oxyacetate, zirconium oxycarbonate, and ammonium zirconium oxycarbonate to obtain a neutralized reaction product, and washing the neutralized reaction product.

The hydroxide of an alkali metal ($M_2O$) used in the above step (1) is, for example, potassium hydroxide, sodium hydroxide, etc. Among them, potassium hydroxide is used preferably.

Preferably, this hydroxide of an alkali metal is added at a molar ratio to the zirconium oxide hydrate ($M_2O/ZrO_2 \cdot xH_2O$) of 1/1 to 10/1.

Preferably, the hydrogen peroxide ($H_2O_2$) used in the above step (1) is added at a molar ratio to the zirconium oxide hydrate ($H_2O_2/ZrO_2 \cdot xH_2O$) of 5/1 to 30/1.

As the silica sol used in the above step (2), any commercially available product (for example, SI-30 manufactured by Catalysts and Chemicals Industries Co., Ltd.) may be used as long as the product contains silica-based fine particles having an average particle size of 2 to 300 nm. The concentration of the silica-based fine particles contained in the silica sol is preferably in the range from 0.5 to 5% by weight.

The aqueous solution of the silicic acid solution (hereinafter sometimes referred to simply as a "silicic acid solution") used in the above step (2) is obtained, for example, by treating an aqueous solution of a silicate, for example, an alkali metal silicate such as sodium silicate (water glass) or potassium silicate, or an organic base silicate such as quaternary ammonium silicate, with a cation-exchange resin to remove alkali cations.

It is preferable to use, among these aqueous solutions of the silicic acid solution, an aqueous solution having a pH of 2 to 4 and a silicon content of 0.5 to 5% by weight in terms of $SiO_2$.

It is preferable that the mixed aqueous solution-(1) obtained in the above step (1) and the silicic acid solution be prepared respectively so that the molar ratio ($ZrO_2/SiO_2$-(1)) is 1/16 to 1/1, when the zirconium components in the mixed aqueous solution-(1) are expressed as $ZrO_2$ and the silicon components contained in the silicic acid solution are expressed as $SiO_2$-(1), and that they be added together slowly into the silica sol.

It is also preferable that the amount of these solutions to be added to the silica sol be in the range of 7/100 to 15/10 in terms of weight ratio $\{(ZrO_2/SiO_2\text{-}(1))/SiO2\text{-}(2)\}$, when the silica-based fine particles are expressed as $SiO_2$-(2), although the amount to be added varies depending on the degree of coating of the silica-based fine particles contained in the silica sol. Preferably, the silica sol is heated previously to a temperature of 70 to 95° C. before these solutions are added.

When the mixed aqueous solution-(1) and the aqueous solution of the silicic acid solution are added under stirring to the silica sol, as described above, the zirconium components and the silicon components undergo hydrolysis reactions in the mixed aqueous solution-(2), and the surfaces of the silica-based fine particles contained in the silica sol are covered with coatings of partial hydrolysates or hydrolysates of the above components.

As the mixed aqueous solution-(1) having strong alkalinity is added to the silica sol, the pH of the mixed aqueous solution-(2) increases with time. Therefore, it is desirable to stop the addition of the mixed aqueous solution-(1) and the silicic acid solution when the pH of the mixed aqueous solution-(2) approaches 11. When the pH exceeds 11, the silica-based fine particles contained in the silica sol begin to be dissolved in the mixed aqueous solution-(2) due to the alkalinity, which is not preferable.

Therefore, if the addition of the mixed aqueous solution-(2) and the silicic acid solution has not yet been completed at the time when the pH reaches 11, it is preferable that the step (3) as described below be performed to remove alkali cations, and then the operation of the step (2) be carried out again or be repeated.

In the step (3), the mixed aqueous solution-(2) obtained in the step (2) is subjected to a treatment with a cation-exchange resin to remove alkali cations. There is no particular limitation on the cation-exchange resin used in this step. It is preferable to use a cation-exchange resin such as SK1BH manufactured by Mitsubishi Chemical Corporation.

In this step, it is preferable that the mixed aqueous solution-(2) be subjected to the above treatment for removing alkali cations so that the mixed aqueous solution-(2) has a pH of 7.0 to 10.0.

In the above step (4), the mixed aqueous solution-(3) obtained in the step (3) is subjected to a hydrothermal treatment in a reaction vessel at a temperature of 100° C. to 350° C. The reaction vessel is not particularly limited as long as it is a pressure and heat resistant vessel capable of withstanding a pressure of 0.5 to 16.5 MPa, and a stainless steel autoclave is used preferably.

Thus, a mixed aqueous solution-(4) containing the filler (B) in which the surfaces of the silica-based fine particles are covered with coatings of an oxide containing at least a zirconium atom, a silicon atom, and an oxygen atom is obtained.

In the step (5), the solid product composed of the filler (B) contained in the mixed aqueous solution-(4) obtained in the step (4) is dried. The solid product contained in the mixed aqueous solution-(4) can be dried by being subjected to a commonly used conventional drying step, for example, a step of filtering the solid product from the mixed aqueous solution-(4), washing the filtered solid product with pure water or distilled water if necessary, and then drying the washed solid product by hot air at a temperature of 80 to 250° C.

It is desirable to subject the dried product obtained in this hot air drying step to a grinding step using a mortar and a ball mill, if necessary, to adjust the particle size. The resulting dried product has a partial structure, as shown in FIG. 1, for example, in which the oxide coating of a silica-based fine particle and the oxide coating of a neighboring silica-based fine particle extend and are connected to each other, and the oxide coatings each cover a plurality of silica-based fine particles. The resulting dried product has, as an overall structure, a porous particle structure, as shown in FIG. 2, for example, in which the oxide coatings are connected to each other to form an aggregate of the silica-based fine particles covered with the oxide coatings.

In the above step (5), the filler (B) of spherical particles in overall shape can be obtained also by spray-drying the mixed aqueous solution-(4) with a spray dryer or the like.

Thus, a dried amorphous powder or a ground product thereof consisting of inorganic oxide fine particles including silica-based fine particles covered with coatings of an oxide containing at least zirconium, silicon, and oxygen is obtained.

The dried amorphous powder or the ground product thereof obtained as above may be used as it is as the filler (B) used in the present invention, but it is preferable that the dried amorphous powder or the ground product thereof be calcined at a temperature of 300 to 900° C. in terms of the mechanical strength and wear resistance. A known method can be used for the calcining without any limitation. Preferably, the dried amorphous powder or the ground product thereof is calcined in a quartz crucible placed in an electric furnace.

The calcined product as the filler (B) (calcined amorphous powder) can be obtained easily by calcining the dried amorphous powder in the manner as described above. The shape of the particles of the calcined product is almost the same as that of the particles of the above-mentioned dried amorphous powder, although some of the particles are contracted.

Accordingly, the calcined product of the filler (B) also can have a porous particle structure in which the oxide coatings are connected to each other to form an aggregate of the silica-based fine particles covered with the oxide coatings. The calcined product obtained in the calcining step may be subjected to the grinding step using a mortar, a ball mill, etc., if necessary, to adjust the particle size.

For the inorganic particles (C) used in the dental composition of the present invention, any known inorganic particles used for dental compositions can be used without any limitation as long as their average particle sizes fall within the range of 0.1 to 1.0 µm. Examples of the inorganic particles include: various kinds of glass powders (containing silica as a main component and further containing an oxide of a heavy metal, boron, aluminum, and the like, if necessary: e.g., glass powders having typical compositions, such as fused silica, quartz, soda lime silica glass, E-glass, C-glass, borosilicate glass (Pyrex (registered trademark) glass); and glass powders for dental use, such as barium glass (GM 27884 and 8235 manufactured by Schott, and Ray-Sorb E-2000 and Ray-Sorb E-3000 manufactured by Specialty Glass), strontium borosilicate glass (Ray-Sorb E-4000 manufactured by Specialty Glass), lanthanum glass ceramics (GM 31684 manufactured by Schott), and fluoroaluminosilicate glass (GM 35429, G018-091, G018-117 manufactured by Schott); various kinds of ceramics; composite oxides such as silica-titania, and silica-zirconia; diatomaceous earth; kaolin; clay minerals (such as montmorillonite); activated white clay; synthetic zeolite; mica; calcium fluoride; ytterbium fluoride; yttrium fluoride; calcium phosphate; barium sulfate; zirconium dioxide; titanium dioxide; hydroxyapatite; and the like. Any one of the above-mentioned inorganic particles can be used alone or as a mixture of two or more kinds thereof. Among them, those containing silica as a main component are used preferably as the inorganic particles (C) in the dental composition of the present invention. In the present invention, the inorganic particles containing silica as a main component are the particles composed of an inorganic material containing at least 25% by weight of silica (preferably at least 40% by weight of silica).

The average particle size of the inorganic particles (C) is 0.1 to 1.0 µm, preferably 0.2 to 0.9 µm, and more preferably 0.4 to 0.7 µm. When the average particle size is less than 0.1 µm, the mechanical strength may be insufficient, or the paste becomes sticky, which may cause insufficient handling properties. When the average particle size exceeds 1.0 µm, the surface smoothness and gloss after polishing and the gloss durability as a cured product are impaired.

Like the filler (B), the inorganic particles (C) are used in combination with the polymerizable monomer (A) for the dental composition. Therefore, it is desirable that the inorganic particles (C) be subjected previously to surface treatment with a surface treating agent to improve the affinity between the inorganic particles (C) and the polymerizable monomer (A), and to increase the chemical bonding between the inorganic particles (C) and the polymerizable monomer (A) so as to enhance the mechanical strength of the composite material. As such a surface treating agent, any one of the organic metal compounds described as examples for the filler (B) can be used likewise.

The average particle size of the inorganic particles (C) can be measured in the same manner as the average particle size of the filler (B) described above.

The shape of the inorganic particles (C) is not particularly limited. The inorganic particles (C) can be used as an irregular-shaped or spherical powder particles. If the irregular-shaped inorganic particles (C) are used, a dental composition having particularly excellent mechanical strength and wear resistance can be obtained, and if the spherical inorganic particles (C) are used, a dental composition having particularly excellent surface smoothness and gloss after polishing and gloss durability can be obtained. The shape of the inorganic particles (C) may be selected suitably in accordance with the intended use of the dental composition.

The refractive index of the inorganic particles (C) is not particularly limited, but if it is approximated to the refractive indices of the polymerizable monomer (A) and the filler (B), the transparency of the cured product of the dental composition can be enhanced easily. Therefore, the refractive index of the inorganic particles (C) is preferably 1.45 to 1.63, more preferably 1.50 to 1.60, and particularly preferably 1.52 to 1.58.

The amount of the inorganic particles (C) to be added is preferably 100 to 400 parts by weight per 100 parts by weight of the polymerizable monomer (A), more preferably 150 to 350 parts by weight, and particularly preferably 150 to 300 parts by weight.

The amount of the inorganic particles (C) to be added is not particularly limited by the amount of the filler (B) to be added. It is preferable, however, to determine the amounts of the filler (B) and the inorganic particles (C) to be added respectively so that the total amount of the filler (B) and the inorganic particles (C) is in the range of 200 to 600 parts by weight per 100 parts by weight of the polymerizable monomer (A). When the total amount of the filler (B) and the inorganic filler (C) is in this range, a dental composition having particularly excellent mechanical strength can be obtained.

The weight ratio between the filler (B) and the inorganic particles (C) also is not particularly limited, but it is preferable that (the weight of the filler (B))/(the weight of the inorganic particles (C)) be 0.2 to 4.0. When the weight ratio between the filler (B) and the inorganic filler (C) is in this range, a dental composition having particularly excellent handling properties can be obtained.

It is preferable that the dental composition of the present invention further contain the inorganic ultrafine particles (D). As the inorganic ultrafine particles (D), any known inorganic ultrafine particles used in dental compositions are used without any limitation. Preferable examples of the inorganic ultrafine particles (D) include particles of inorganic oxides such as silica, alumina, titania, zirconia, particles of composite oxides of any of these oxides, and particles of calcium phosphate, hydroxyapatite, yttrium fluoride, ytterbium fluoride, and the like. Preferably, the inorganic ultrafine particles (D) are particles of silica, alumina, titania, or the like prepared by flame pyrolysis, and examples thereof include products manufactured by Japan Aerosil Co., Ltd. under the trade names of Aerosil, Aeroxide Alu C, Aeroxide $TiO_2$ P 25, Aeroxide $TiO_2$ P 25S, VP Zirconium Oxide 3-YSZ, and VP Zirconium Oxide 3-YSZ PH.

The average particle size of the inorganic ultrafine particles (D) is 5 to 50 nm, and preferably 10 to 40 nm. The amount of the inorganic ultrafine particles (D) to be added is preferably 10 to 50 parts by weight per 100 parts by weight of the polymerizable monomer (A). The average particle size of the inorganic ultrafine particles (D) can be measured in the same manner as the average particle size of the silica-based fine particles described above.

Like the filler (B) and the inorganic particles (C), the inorganic ultrafine particles (D) are used in combination with the polymerizable monomer (A) for the dental composition. Therefore, it is desirable that the inorganic ultrafine particles (D) be subjected previously to surface treatment with a surface treating agent to improve the affinity between the inorganic ultrafine particles (D) and the polymerizable monomer (A), and to increase the chemical bonding between the inorganic ultrafine particles (D) and the polymerizable monomer (A) so as to enhance the mechanical strength of the composite material. As the surface treating agent, any one of the organic metal compounds described as examples for the filler (B) can be used likewise.

The polymerizable monomer (A) can be polymerized by a known method. It is preferable that the dental composition of the present invention further contain a polymerization initiator. The polymerization initiator can be selected from polymerization initiators commonly used in the industrial field. Among them, polymerization initiators used for dental applications are used preferably. Particularly, photopolymerization initiators and chemical polymerization initiators are used alone, or two or more of them are used in suitable combination.

Examples of the photopolymerization initiator include (bis)acylphosphine oxides, water-soluble acylphosphine oxides, thioxanthones or quaternary ammonium salts of thioxanthones, ketals, α-diketones, benzoin alkyl ether compounds, and α-amino ketone compounds.

Among (bis)acylphosphine oxides used as the photopolymerization initiator, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

Preferably, the water-soluble acylphosphine oxides used as the photopolymerization initiator have alkali metal ions, alkaline earth metal ions, pyridinium ions, or ammonium ions in the acylphosphine oxide molecules. For instance, the water-soluble acylphosphine oxides can be synthesized by the method disclosed in EP 0009348 B1 or JP 57 (1982)-197289A.

Specific examples of the aforementioned water-soluble acylphosphine oxides include sodium monomethylacetylphosphonate, sodium monomethyl(1-oxopropyl)phosphonate, sodium monomethylbenzoylphosphonate, sodium monomethyl(1-oxobutypphosphonate, sodium monomethyl(2-methyl-1-oxopropyl)phosphonate, sodium acetylphosphonate, sodium monomethylacetylphosphonate, sodium acetylmethylphosphonate, methyl-4-(hydroxymethoxyphosphinyl)-4-oxobutanoate sodium salt, methyl-4-oxophosphonobutanoate monosodium salt, acetylphenylphosphinate sodium salt, sodium (1-oxopropyl)pentylphosphinate, methyl-4-(hydroxypentylphosphinyl)-4-oxobutanoate sodium salt, sodium acetylpentylphosphinate, sodium acetylethylphosphinate, sodium methyl(1,1-dimethyl)methylphosphinate, sodium (1,1-diethoxyethyl)methylphosphinate, sodium (1,1-diethoxyethypmethylphosphinate, methyl-4-(hydroxymethylphosphinyl)-4-oxobutanoate lithium salt, 4-(hydroxymethylphosphinyl)-4-oxobutanoic acid dilithium salt, methyl(2-methyl-1,3-dioxolan-2-yl)phosphinate sodium salt, methyl(2-methyl-1,3-thiazolidin-2-yl)phosphonite sodium salt, (2-methylperhydro-1,3-diazin-2-yl)phosphonite sodium salt, acetylphosphinate sodium salt, (1,1-diethoxyethyl)phosphonite sodium salt, (1,1-diethoxyethyl)methylphosphonite sodium salt, methyl(2-methyloxathiolane-2-yl)phosphinate sodium salt, methyl(2,4,5-trimethyl-1,3-dioxolan-2-yl)phosphinate sodium salt, methyl(1,1-propoxyethyl)phosphinate sodium salt, (1-methoxyvinyl)methylphosphinate sodium salt, (1-ethylthiovinyl)methylphosphinate sodium salt, methyl(2-methylperhydro-1,3-diazin-2-yl)phosphinate sodium salt, methyl(2-methylperhydro-1,3-thiazin-2-yl)phosphinate sodium salt, methyl(2-methyl-1,3-diazolidin-2-yl)phosphinate sodium salt, methyl(2-methyl-1,3-thiazolidin-2-yl)phosphinate sodium salt, (2,2-dicyano-1-methylethynyl)phosphinate sodium salt, acetylmethylphosphinate oxime sodium salt, acetylmethylphosphinate-O-benzyloxime sodium salt, 1-[N-ethoxyimino)ethyl]methylphosphinate sodium salt, methyl (1-phenyliminoethyl)phosphinate sodium salt, methyl(1-phenylhydrazone ethyl)phosphinate sodium salt, [1-(2,4-dinitrophenylhydrazono)ethyl]methylphosphinate sodium salt, acetylmethylphosphinate semicarbazone sodium salt, (1-cyano-1-hydroxyethypmethylphosphinate sodium salt, (dimethoxymethyl)methyl phosphinate sodium salt, formylmethylphosphinate sodium salt, (1,1-dimethoxypropyl)methylphosphinate sodium salt, methyl(1-oxopropyl)phosphinate sodium salt, dodecylguanidine salt of (1,1-dimethoxypropyl)methylphosphinate, isopropylamine salt of (1,1-dimethoxypropyl)methylphosphinate, acetylmethylphosphinate thiosemicarbazone sodium salt, 1,3,5-tributyl-4-methylamino-1,2,4-triazolium (1,1-dimethoxyethyl)-methylphosphinate, 1-butyl-4-butylaminomethylamino-3,5-dipropyl-1,2,4-triazolium (1,1-dimethoxyethyl)-methylphosphinate, 2,4,6-trimethylbenzoylphenylphosphine oxide sodium salt, 2,4,6-trimethylbenzoylphenylphosphine oxide potassium salt, and ammonium salt of 2,4,6-trimethylbenzoylphenylphosphine oxide. Furthermore, examples thereof also include compounds described in JP 2000-159621 A.

Among these (bis)acylphosphine oxides and water-soluble acylphosphine oxides, particularly preferable ones are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt.

Examples of thioxanthones or the quaternary ammonium salts of thioxanthones that are used as the above-mentioned photopolymerization initiators include thioxanthone, 2-chlorothioxanthen-9-one, 2-hydroxy-3-(9-oxy-9H-thioxanthen-4-yloxy)-N,N,N-trimethyl-propaneaminium chloride, 2-hydroxy-3-(1-methyl-9-oxy-9H-thioxanthen-4-yloxy)-N,N,N-trimethyl-propaneaminium chloride, 2-hydroxy-3-(9-oxo-9H-thioxanthen-2-yloxy)-N,N,N-trimethyl-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Among the thioxanthones or the quaternary ammonium salts of thioxanthones, a particularly preferable thioxanthone is 2-chlorothioxanthen-9-one, and a particularly preferable quaternary ammonium salt of thioxanthone is 2-hydroxy-3-(3,4-dimethyl-9H-thioxanthen-2-yloxy)-N,N,N-trimethyl-1-propaneaminium chloride.

Examples of ketals used as the photopolymerization initiator include benzyl dimethyl ketal and benzyl diethyl ketal.

Examples of the α-diketones used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferable from the viewpoint of having the maximum absorption wavelength in the visible light range.

Examples of the benzoin alkyl ethers used as the aforementioned photopolymerization initiator include benzoin methyl ether, benzoin ethyl ether, benzoin isopropyl ether, and benzoin isobutyl ether.

Examples of the α-aminoketones used as the aforementioned photopolymerization initiator include 2-methyl-1-[4-(methylthio)phenyl]-2-morpholinopropan-1-one.

Preferably, among these photopolymerization initiators, at least one selected from the group consisting of (bis)acylphosphine oxides, salts thereof, and α-diketones is used. This makes it possible to obtain a composition that has excellent photocurability in visible and near-ultraviolet ranges and sufficiently high photocurability regardless of which light source among a halogen lamp, light-emitting diode (LED), and xenon lamp is used.

Among the polymerization initiators used in the present invention, a chemical polymerization initiator that is used preferably is organic peroxide. The organic peroxide used as the chemical polymerization initiator is not particularly limited and a known one can be used. Examples of typical organic peroxides include ketone peroxide, hydroperoxide, diacyl peroxide, dialkyl peroxide, peroxyketal, peroxyester, and peroxydicarbonate.

Examples of the ketone peroxide used as the chemical polymerization initiator include methyl ethyl ketone peroxide, methyl isobutyl ketone peroxide, methylcyclohexanone peroxide, and cyclohexanone peroxide.

Examples of the hydroperoxide used as the chemical polymerization initiator include 2,5-dimethylhexane-2,5-dihydroperoxide, diisopropylbenzene hydroperoxide, cumene hydroperoxide, and t-butyl hydroperoxide.

Examples of the diacyl peroxide used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxide used as the chemical polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketal used as the chemical polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and 4,4-bis(t-butylperoxy)valeric acid-n-butyl ester.

Examples of the peroxyester used as the chemical polymerization initiator include α-cumyl peroxyneodecanoate, t-butyl peroxyneodecanoate, t-butyl peroxypivarate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethyl hexanoate, t-butylperoxy acetate, t-butylperoxy benzoate, and t-butylperoxymaleic acid.

Examples of the peroxydicarbonate used as the chemical polymerization initiator include di-3-methoxy peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, diacyl peroxides are used preferably from the viewpoint of a comprehensive balance of safety, storage stability, and radical production ability, and among these, benzoyl peroxide is used particularly preferably.

The amount of the polymerization initiator to be added in the present invention is not particularly limited. However, from the viewpoint of, for example, curability of the resultant composition, it is preferable that 0.01 to 10 parts by weight of the polymerization initiator be contained per 100 parts by weight of the polymerizable monomer component (A), and it is more preferable that 0.1 to 5 parts by weight of the polymerization initiator be contained. When the amount of the polymerization initiator is less than 0.01 part by weight, polymerization may not proceed sufficiently and thereby mechanical strength may be reduced. Therefore, the amount is more preferably at least 0.1 part by weight. On the other hand, when the amount of the polymerization initiator exceeds 10 parts by weight, in the case where the polymerization initiator itself has low polymerization performance, sufficient mechanical strength may not be obtained and furthermore precipitation from the composition may occur. Therefore, the amount is more preferably 5 parts by weight or less.

In a preferred embodiment, a polymerization accelerator is used. Examples of the polymerization accelerator used in the present invention include amines, sulfinic acids and salts thereof, aldehydes, and thiol compounds.

Amines used as the polymerization accelerator can be divided into aliphatic amines and aromatic amines. Examples of aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferable from the viewpoint of curability and storage stability of the composition, and particularly, N-methyldiethanolamine and triethanolamine are used more preferably.

Examples of aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic acid 2-(methacryloyloxy)ethyl ester, 4-N,N-dimethylaminobenzophenone, and butyl 4-dimethylaminobenzoate. Among these, at least one selected from the group consisting of N,N-di(2-hydroxyethyl)-p-toluidine, 4-N,N-dimethylaminobenzoic acid ethyl ester, N,N-dimethylaminobenzoic acid n-butoxyethyl ester, and 4-N,N-dimethylaminobenzophenone is used preferably from the viewpoint of being capable of providing the composition with excellent curability.

Examples of the sulfinic acid or salt thereof used as the polymerization accelerator include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Sodium benzenesulfinate, sodium p-toluenesulfinate, and sodium 2,4,6-triisopropylbenzenesulfinate are particularly preferable.

Examples of aldehydes used as the polymerization accelerator include derivatives of terephthalaldehyde and benzaldehyde. Examples of the benzaldehyde derivative include dimethylaminobenzaldehyde, p-methyloxybenzaldehyde, p-ethyloxybenzaldehyde, and p-n-octyloxybenzaldehyde. Among these, from the viewpoint of curability, p-n-octyloxybenzaldehyde is used preferably.

Examples of the thiol compound used as the polymerization accelerator include 3-mercaptopropyltrimethoxysilane, 2-mercaptobenzoxazole, decanethiol, and thiobenzoic acid.

The amount of polymerization accelerator to be added in the present invention is not particularly limited. However, from the viewpoints of, for example, curability of the resultant composition, it is preferable that 0.001 to 10 parts by weight of polymerization accelerator be contained per 100 parts by weight of the polymerizable monomer component (A), and it is more preferable that 0.001 to 5 parts by weight of the polymerization accelerator be contained. When the amount of the polymerization accelerator is less than 0.001 part by weight, polymerization may not proceed sufficiently and mechanical strength may be reduced. Therefore, the amount is more preferably at least 0.05 part by weight. On the other hand, when the amount of the polymerization accelerator exceeds 10 parts by weight, in the case where the polymerization initiator itself has low polymerization performance, sufficiently high mechanical strength may not be obtained. Therefore, the amount is more preferably 5 parts by weight or less.

To the curable dental composition of the present invention, a pH adjuster, an ultraviolet absorber, an antioxidant, a polymerization inhibitor, a colorant, an antibacterial agent, an X-ray contrast agent, a thickening agent, a fluorescent agent, or the like can further be added in accordance with the intended use.

For example, when the cured surface is expected to have a fluorine ion sustained-release property, a fluorine ion sustained-releasable filler, such as fluoroaluminosilicate glass, calcium fluoride, sodium fluoride, or sodium monofluorophosphate also can be added.

When it is expected to have an antibacterial property, for example, a surfactant having an antibacterial activity, such as cetylpyridinium chloride or 12-(meth)acryloyloxydodecylpyridinium bromide, or a photocatalytic titanium oxide can be added.

According to the present invention in which the special filler (B) and the inorganic particles (C) each having an average particle size in a specified range are used in combination in the dental composition, a cured product having high mechanical strength can be obtained. As described above, the dental composition of the present invention contains the inorganic particles (C) having the average particle size in the specified range in addition to the special filler (B) capable of increasing the handling properties, mechanical strength, and polishability. Therefore, higher mechanical strength can be obtained without impairing the surface smoothness and gloss after polishing and the gloss durability. Furthermore, since the cured product has high surface smoothness and gloss after polishing and high gloss durability, the dental material using the dental composition of the present invention has a good aesthetic appearance. Furthermore, the dental composition of the present invention has good handling properties as well as proper fluidity and forming property as a paste, and the adhesion to dental instruments and stickiness are reduced. That is, the dental composition is very easy to handle.

The dental composition of the present invention can be used suitably in a conventional manner as dental materials, for example, dental composite resins such as dental composite filling materials, dental crown materials, and luting materials, dental adhesives such as orthodontic adhesives, cavity coating adhesives, and dental fissure sealing materials, denture base materials, tissue conditioning materials for denture bases, fissure sealants, coating materials applied to tooth surfaces and dental prostheses, surface glazing materials, and dental lacquers. The cured product obtained by polymerizing and curing the dental composition of the present invention also can be used as artificial teeth, dentures, and resin blocks for CAD/CAM. Among them, the dental composition of the present invention can be used advantageously as a dental composite resin. This composite resin exhibits excellent surface smoothness and gloss after polishing and gloss durability as a cured product as well as good handling properties as a paste.

EXAMPLES

The present invention will be described in more detail below by the following examples, without intending to limit the scope of the present invention to these examples. The test methods, materials, etc. used in the examples are shown below.

[Measurement of Particle Size of Powder]

A laser diffraction particle size distribution analyzer (SALD-2100 manufactured by Shimadzu Corporation) was used to measure the particle size of each of the produced powders. As a dispersion medium, a 0.2% aqueous solution of sodium hexametaphosphate was used.

[Handling properties]

The produced dental composition was filled in a cavity of 4 mm$\phi$×4 mm, and the handling properties of the composition as a paste were evaluated, in terms of ease of filling, according to the following evaluation criteria.

5: The paste has a particularly excellent forming property, spreads well, and is not sticky. Very easy to fill.

4: The paste has an excellent forming property, spreads well, and is not sticky. Very easy to fill.

3: The paste is shapable, spreads sufficiently, and is not sticky. Easy to fill.

2: Either the forming property or spreading of the paste is insufficient, or the paste is sticky. Difficult to fill.

1: The forming property, spreading, and stickiness are all insufficient for practical use. Not suitable for practical use in terms of filling operation.

The pastes rated 3, 4, and 5 are suitable for practical use.

[Compressive Strength]

A test sample (4 mm$\phi$×4 mm) of the cured product of the produced dental composition was prepared. The test sample was immersed in water at 37° C. for 24 hours. The compressive strength of the test sample was measured using a universal testing machine (manufactured by Instron) with the crosshead speed being set at 2 mm/min.

[Flexural Strength of Cured Product]

A test sample (2 mm×2 mm×30 mm) of the cured product of the produced dental composition was prepared. The test sample was immersed in water at 37° C. for 24 hours. The flexural strength of the test sample was measured using a universal testing machine (manufactured by Instron) with the span being set at 20 mm and the crosshead speed being set at 1 mm/min according to a three-point flexural test method.

[Polishability]

The produced dental composition was filled in a stainless steel mold (with a thickness of 1 mm and a diameter of 15 mm). The mold was clamped between upper and lower glass slides and the upper and lower surfaces of the mold were each exposed to light irradiation for 2 minutes with a visible light irradiator for dental laboratories ($\alpha$-light II, manufactured by J. Morita Mfg. Corp). Thus, the dental composition was cured. The cured product was taken out of the mold, and then one surface of the cured product was polished with a #800 waterproof abrasive paper. Then, this polished surface was buffed with a dental polishing kit (EWL 80, manufactured by KAYO) at 3000 rpm for 20 seconds. As a polishing material, Porceny Hydron (manufactured by Tokyo Shizaisha) was used. The gloss of the polished surface was measured with a glossmeter (VG-107, manufactured by Nippon Denshoku Industries Co., Ltd.) and indicated as a ratio to the specular gloss of 100%. The measurement was performed at an angle of 60 degrees. Preferably, the degree of gloss is 70% or more.

Preparation Example 1

Preparation of Filler B-1

250 kg of zirconium oxychloride ($ZrOCl_2.8H_2O$, manufactured by Taiyo Koko Co., Ltd.) was added to 4375 kg of pure water at a temperature of 15° C. and they were stirred to dissolve zirconium oxychloride therein.

250 L of aqueous ammonia with a concentration of 15% by weight was added slowly, under stirring, to the aqueous solution of zirconium oxychloride to cause a neutralization reaction of the zirconium oxychloride under the temperature condition of 15° C. Thus, a slurry containing the precipitate of zirconium oxide hydrate was obtained. The pH of this slurry was 8.5.

Next, this slurry was filtered, and the resulting cake-like material was washed repeatedly with pure water to remove by-products of the neutralization reaction and unreacted substances. As a result, 860 kg of a cake-like material consisting of 10% by weight of zirconium oxide hydrate in terms of $ZrO_2$ and water was obtained.

Next, 45800 g of pure water was added to 5416 g of the cake-like material containing zirconium oxide hydrate, and further 1024 g of potassium hydroxide with a purity of 85% (manufactured by Kanto Chemical Co., Inc.) was added under stirring to the above mixture to make the mixture alkaline. Then, 10248 g of hydrogen peroxide solution containing 35% by weight of hydrogen peroxide (manufactured by Hayashi Pure Chemical Industries, Ltd.) was added to the mixture.

Furthermore, this mixed aqueous solution was allowed to stand, under stirring, for one hour to peptize the zirconium oxide hydrate in the aqueous solution. Then, 39991 g of ice water obtained by freezing pure water was added to the resulting aqueous solution to cool the temperature of the aqueous solution, which had been raised by the exothermic reaction, to 30° C. or lower. As a result, 102400 g of a mixed aqueous solution (hereinafter referred to as a "prepared solution 1A") with a pH of about 11 and containing 0.5% by weight of zirconium components in terms of $ZrO_2$ was obtained.

10 Kg of commercially available water glass (manufactured by AGC Si-Tec. Co., Ltd.) was diluted with 38 kg of pure water, and then was treated with a cation-exchange resin (manufactured by Mitsubishi Chemical Corporation) to remove alkali cations contained therein. Thus, 9 kg of a silicic acid solution with a pH of 3 and containing 4% by weight of $SiO_2$ was prepared. Then, 10768 g of the silicic acid solution and 14860 g of pure water were mixed with each other to prepare 25628 g of a silicic acid solution containing 2% by weight of $SiO_2$.

Next, 47900 g of pure water was added to 3336 g of a silica sol containing 30% by weight of silica-based fine particles having an average particle size of 12 nm (SI-30, manufactured by Catalysts and Chemicals Industries Co., Ltd.), and the resulting mixture was stirred sufficiently. Thus, 51236 g of a silica sol containing 2% by weight of silica-based fine particles was obtained.

Next, the silica sol was heated to 90° C., and then 51200 g of the prepared solution 1A and 12814 g of the aqueous solution of the silicic acid solution were added slowly under stirring to the silica sol over 10 hours. As a result, 115250 g of a mixed aqueous solution with a pH of about 11 (hereinafter referred to as a prepared solution 1B-(1)) was obtained.

Next, the prepared solution 1B-(1) was treated with a cation-exchange resin (SK1BH, manufactured by Mitsubishi Chemical Corporation) to remove alkali cations contained therein. As a result, 117250 g of a mixed aqueous solution with a pH of about 9.5 (hereinafter referred to as a prepared solution 1C-(1)) was obtained.

Furthermore, 51200 g of the prepared solution 1A and 12814 g of the aqueous solution of the silicic acid solution were added slowly to the prepared solution 1C-(1) over 10 hours in the same manner as described above. As a result, 181264 g of a mixed aqueous solution with a pH of about 11 (hereinafter referred to as a prepared solution 1B-(2)) was obtained.

Next, the prepared solution 1B-(2) was treated with a cation-exchange resin (SK1BH, manufactured by Mitsubishi Chemical Corporation) to remove alkali cations contained therein. As a result, 182264 g of a mixed aqueous solution with a pH of about 9.5 (hereinafter referred to as a prepared solution 1C-(2)) was obtained.

Next, 100200 g of the prepared solution 1C-(2) was put in a stainless steel autoclave (manufactured by Taiatsu Techno Corporation), and was subjected to a hydrothermal treatment for 18 hours at a temperature of 165° C. As a result, 99750 g of a mixed aqueous solution (hereinafter referred to as a prepared solution 1D) was obtained. This aqueous solution contained a filler in which the surfaces of silica-based fine particles were covered with coatings of an oxide containing a zirconium atom, a silicon atom, and an oxygen atom.

Next, the prepared solution 1D was pre-dried in a hot air dryer at 90° C. to obtain a pre-dried solid material 1B. This pre-dried solid material 1B was dried for another hour at 200° C., and then ground in a vibratory ball mill for 1.5 hours. Thus, a dried amorphous powder having an average particle size of 4.9 µm was obtained. 100 parts by weight of this dried amorphous powder was subjected to surface treatment with 30 parts by weight of γ-methacryloxypropyltrimethoxysilane. As a result, a filler B-1 was obtained. There was no substantial change in the average particle size of the filler B-1 before and after the surface treatment.

Preparation Example 2

Preparation of Filler B-2

The pre-dried solid substance 1B obtained in Preparation Example 1 was placed in an electric furnace at 800° C. and subjected to heat treatment for 1 hour to obtain a calcined solid material 2B. This calcined solid material 2B was ground in a vibratory ball mill for 1.5 hours. Thus, a calcined amorphous powder having an average particle size of 6.3 µm was obtained. 100 parts by weight of the calcined amorphous powder thus obtained was subjected to surface treatment with 30 parts by weight of γ-methacryloxypropyltrimethoxysilane. As a result, a filler B-2 was obtained. There was no substantial change in the average particle size of the filler B-2 before and after the surface treatment.

Preparation Example 3

Preparation of Filler B-3

The calcined solid material 2B obtained in Preparation Example 2 was ground in a vibratory ball mill for 24 hours. Thus, a calcined amorphous powder having an average particle size of 1.9 µm was obtained. 100 parts by weight of the calcined amorphous powder thus obtained was subjected to surface treatment with 40 parts by weight of γ-methacryloxypropyltrimethoxysilane. As a result, a filler B-3 was obtained. There was no substantial change in the average particle size of the filler B-3 before and after the surface treatment.

Preparation Example 4

Preparation of Filler B-4

The calcined solid material 2B obtained in Preparation Example 2 was ground in a vibratory ball mill for 1 hour. Thus, a calcined amorphous powder having an average particle size of 18.2 µm was obtained. 100 parts by weight of the calcined amorphous powder thus obtained was subjected to surface treatment with 20 parts by weight of γ-methacryloxypropyltrimethoxysilane. As a result, a filler B-4 was obtained. There was no substantial change in the average particle size of the filler B-4 before and after the surface treatment.

Preparation Example 5

Preparation of Filler B-5

The calcined solid material 2B obtained in Preparation Example 2 was ground in a vibratory ball mill for 72 hours. Thus, a calcined amorphous powder having an average particle size of 0.7 µm was obtained. 100 parts by weight of the calcined amorphous powder thus obtained was subjected to surface treatment with 45 parts by weight of γ-methacryloxypropyltrimethoxysilane. As a result, a filler B-5 was obtained. There was no substantial change in the average particle size of the filler B-5 before and after the surface treatment.

Preparation Example 6

Preparation of Filler B-6

The calcined solid material 2B obtained in Preparation Example 2 was ground in a vibratory ball mill for 30 minutes. Thus, a calcined amorphous powder having an average particle size of 25.4 µm was obtained. 100 parts by weight of the calcined amorphous powder thus obtained was subjected to surface treatment with 20 parts by weight of γ-methacryloxypropyltrimethoxysilane. As a result, a filler B-6 was obtained. There was no substantial change in the average particle size of the filler B-6 before and after the surface treatment.

Preparation Example 7

Preparation of Filler B-7

A pH-adjusted silica sol (with a pH of 2.5) prepared by adding dilute nitric acid to 147 g of a commercially available silica sol (Cataloid SI-30 having an average particle size of 10 to 14 nm, manufactured by Catalysts and Chemicals Industries Co. Ltd.), was added slowly dropwise to 85 g of zirconium acetate (zirconium acetate containing 15 to 16% Zr, manufactured by Sigma-Aldrich Corporation) to obtain a mixed sol. The mixed sol thus obtained was put into a stainless steel tray, and then dried in a hot air dryer at 90° C. A solid material obtained by drying the sol was put into an alumina crucible and subjected to heat treatment in an electric furnace at 550° C. for 1 hour, and then the resulting solid material was ground in a vibratory ball mill for 90 minutes. After the grinding, an aggregated silica-zirconia powder having an average particle size of 6.1 μm was obtained. 100 parts by weight of the aggregated powder thus obtained was subjected to surface treatment with 20 parts by weight of γ-methacryloyloxypropyltrimethoxysilane. As a result, a filler B-7 was obtained. There was no substantial change in the average particle size of the filler B-7 before and after the surface treatment.

Preparation Example 8

Preparation of Filler B-8

The calcined solid material 2B obtained in Preparation Example 2 was ground in a vibratory ball mill for 1.5 hours. Thus, a calcined amorphous powder having an average particle size of 6.3 μm was obtained. 100 parts by weight of the porous powder thus obtained was subjected to surface treatment with 25 parts by weight of 11-methacryloyloxyundecyltrimethoxysilane. As a result, a filler B-8 was obtained. There was no substantial change in the average particle size of the filler B-8 before and after the surface treatment.

Preparation Example 9

Preparation of Inorganic Particles C-1

100 parts by weight of barium glass (8235UF 0.7, manufactured by Schott) was subjected to surface treatment with 4 parts by weight of γ-methacryloxypropyltrimethoxysilane. As a result, inorganic particles C-1 having an average particle size of 0.7 μm were obtained.

Preparation Example 10

Preparation of Inorganic Particles C-2

100 parts by weight of barium glass (8235UF 0.4, manufactured by Schott) was subjected to surface treatment with 8 parts by weight of γ-methacryloxypropyltrimethoxysilane. As a result, inorganic particles C-2 having an average particle size of 0.4 μm were obtained.

Preparation Example 11

Preparation of Inorganic Particles C-3

Barium glass (8235UF 0.4, manufactured by Schott) was ground in a vibratory ball mill for 24 hours to obtain inorganic particles having an average particle size of 0.2 μm. 100 parts by weight of the inorganic particles thus obtained were subjected to surface treatment with 10 parts by weight of γ-methacryloxypropyltrimethoxysilane. As a result, inorganic particles C-3 having an average particle size of 0.2 μm were obtained.

Preparation Example 12

Inorganic Particles C-4

100 parts by weight of barium glass (8235UF 1.5, manufactured by Schott) was subjected to surface treatment with 1 part by weight of γ-methacryloxypropyltrimethoxysilane. As a result, inorganic particles C-4 having an average particle size of 1.5 μm were obtained.

Preparation Example 13

Inorganic Particles C-5

100 parts by weight of barium glass (GM27884 NanoFine 180, having a particle size ranging from 0.05 to 0.5 μm and an average particle size of 0.18 μm, manufactured by Schott) was subjected to surface treatment with 10 parts by weight of γ-methacryloxypropyltrimethoxysilane. As a result, inorganic particles C-3 having an average particle size of 0.18 μm were obtained.

Preparation Example 14

Preparation of Inorganic Ultrafine Particles D-1

100 parts by weight of nearly spherical ultrafine particles having an average particle size of 20 nm (Aerosil 130, manufactured by Nippon Aerosil Corporation) were subjected to surface treatment with 40 parts by weight of γ-methacryloxypropyltrimethoxysilane. As a result, inorganic ultrafine particles D-1 were obtained. There was no substantial change in the average particle size of the inorganic ultrafine particles D-1 before and after the surface treatment.

Preparation Example 15

Preparation of Inorganic Ultrafine Particles D-2

100 parts by weight of nearly spherical ultrafine particles having an average particle size of 40 nm (Aerosil OX 50, manufactured by Nippon Aerosil Corporation) were subjected to surface treatment with 7 parts by weight of γ-methacryloxypropyltrimethoxysilane. As a result, inorganic ultrafine particles D-2 were obtained. There was no substantial change in the average particle size of the inorganic ultrafine particles D-2 before and after the surface treatment.

Preparation Example 16

Preparation of Inorganic Ultrafine Particles D-3

100 parts by weight of nearly spherical ultrafine particles having an average particle size of 20 nm (Aeroxide AluC, manufactured by Nippon Aerosil Corporation) were subjected to surface treatment with 20 parts by weight of γ-methacryloyloxypropyltrimethoxysilane. As a result, inorganic ultrafine particles D-3 were obtained. There was no substantial change in the average particle size of the inorganic ultrafine particles D-3 before and after the surface treatment.

Preparation Example 17

Preparation of Inorganic Ultrafine Particles D-4

100 parts by weight of nearly spherical ultrafine particles having an average particle size of 7 nm (Aerosil 380, manufactured by Nippon Aerosil Corporation) were subjected to surface treatment with 50 parts by weight of γ-methacryloyloxypropyltrimethoxysilane. As a result, inorganic ultrafine particles D-4 were obtained. There was no substantial change in the average particle size of the inorganic ultrafine particles D-4 before and after the surface treatment.

Examples 1 to 28 and Comparative Examples 1 to 7

75 parts by weight of 2,2-bis[4-(3-methacryloyloxy-2-hydroxypropoxy)phenyl]propane (referred to as Bis-GMA), 25 parts by weight of triethylene glycol dimethacrylate (referred to as 3G), 0.5 part by weight of α-camphorquinone as a polymerization initiator, and 1.0 part by weight of ethyl N,N-dimethylaminobenzoate as a polymerization accelerator were dissolved to prepare the polymerizable monomer (A).

The amorphous powder (B), the inorganic particles (C), and the inorganic ultrafine particles (D) were mixed with 100 parts by weight of the polymerizable monomer (A) thus obtained, and the mixture was kneaded homogeneously and vacuum-degassed. As a result, the dental compositions of Examples 1 to 28 shown in Tables 1 and 2 and of Comparative Examples 1 to 7 shown in Table 3 were obtained.

TABLE 1

| | | | Examples | | | | | | | | | | | | | | | |
|---|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 | 16 |
| Components of dental composition | Polymerizable monomer (A) | | 100 | 100 | 100 | 100 | 100 | 100 | 100 | 100 | 100 | 100 | 100 | 100 | 100 | 100 | 100 | 100 |
| | Filler (B) | B-1 | 200 | | | | | | | | | | | | | | | |
| | | B-2 | | 200 | | | 200 | 200 | 150 | 150 | 150 | 150 | 50 | 400 | 100 | 200 | 100 | 200 |
| | | B-3 | | | 200 | | | | | | | | | | | | | |
| | | B-4 | | | | 200 | | | | | | | | | | | | |
| | Inorganic particles (C) | C-1 | 200 | 200 | 200 | 200 | | | 150 | 150 | 150 | 150 | 200 | 100 | 100 | 400 | 200 | 100 |
| | | C-2 | | | | | 200 | | | | | | | | | | | |
| | | C-3 | | | | | | 200 | | | | | | | | | | |
| | Inorganic ultrafine particles (D) | D-1 | | | | | | | 20 | 10 | 50 | | | | | | | |
| | | D-2 | | | | | | | | | | 20 | | | | | | |
| Weight of (B)/Weight of (C) | | | 1 | 1 | 1 | 1 | 1 | 1 | 1 | 1 | 1 | 1 | 0.25 | 4 | 1 | 0.5 | 0.5 | 2 |
| Handling properties | | | 4 | 5 | 4 | 4 | 4 | 4 | 5 | 5 | 5 | 5 | 3 | 3 | 4 | 3 | 4 | 4 |
| Compressive strength (MPa) | | | 391 | 414 | 393 | 420 | 404 | 392 | 399 | 394 | 397 | 401 | 412 | 389 | 386 | 461 | 396 | 391 |
| Flexural strength (MPa) | | | 139 | 147 | 138 | 155 | 141 | 139 | 140 | 138 | 142 | 141 | 150 | 134 | 130 | 165 | 142 | 139 |
| Polishability (%) | | | 83 | 83 | 86 | 80 | 82 | 83 | 80 | 81 | 80 | 80 | 79 | 82 | 81 | 75 | 82 | 83 |

TABLE 2

| | | | Examples | | | | | | | | | | | |
|---|---|---|---|---|---|---|---|---|---|---|---|---|---|---|
| | | | 17 | 18 | 19 | 20 | 21 | 22 | 23 | 24 | 25 | 26 | 27 | 28 |
| Components of dental composition | Polymerizable monomer (A) | | 100 | 100 | 100 | 100 | 100 | 100 | 100 | 100 | 100 | 100 | 100 | 100 |
| | Filler (B) | B-1 | | | | | | | | | | | | |
| | | B-2 | 400 | | | | 200 | 150 | 200 | 200 | 300 | 300 | 200 | 300 |
| | | B-3 | | | | | | | | | | | | |
| | | B-4 | | | | | | | | | | | | |
| | | B-8 | | 200 | 200 | 200 | | | | | | | | |
| | Inorganic particles (C) | C-1 | 200 | | | 200 | 200 | 150 | 200 | 200 | 100 | 100 | | |
| | | C-2 | | 200 | | | | | | | | | | |
| | | C-3 | | | 200 | | | | | | | | | |
| | | C-5 | | | | | | | | | | | 200 | 100 |
| | Inorganic ultrafine particles (D) | D-1 | | | | 20 | 5 | 100 | | | | 20 | | 20 |
| | | D-2 | | | | | | | | | 20 | | | |
| | | D-3 | | | | | | | | 20 | | | | |
| | | D-4 | | | | | | | 20 | | | | | |
| Weight of (B)/Weight of (C) | | | 2 | 1 | 1 | 1 | 1 | 1 | 1 | 1 | 3 | 3 | 1 | 3 |
| Handling properties | | | 3 | 4 | 4 | 5 | 4 | 3 | 5 | 5 | 4 | 5 | 4 | 5 |
| Compressive strength (MPa) | | | 398 | 406 | 401 | 415 | 421 | 386 | 429 | 417 | 408 | 413 | 410 | 414 |
| Flexural strength (MPa) | | | 141 | 141 | 139 | 142 | 149 | 139 | 148 | 150 | 148 | 152 | 142 | 147 |
| Polishability (%) | | | 76 | 83 | 84 | 82 | 80 | 81 | 80 | 83 | 84 | 84 | 84 | 83 |

TABLE 3

|  |  |  | Comparative Examples | | | | | | |
|---|---|---|---|---|---|---|---|---|---|
|  |  |  | 1 | 2 | 3 | 4 | 5 | 6 | 7 |
| Components of dental composition | Polymerizable monomer (A) |  | 100 | 100 | 100 | 100 | 100 | 100 | 100 |
|  | Filler (B) | B-1 |  |  |  |  |  |  |  |
|  |  | B-2 |  | 400 |  |  | 200 | 200 |  |
|  |  | B-3 |  |  |  |  |  |  |  |
|  |  | B-4 |  |  |  |  |  |  |  |
|  |  | B-5 |  |  | 200 |  |  |  |  |
|  |  | B-6 |  |  |  | 200 |  |  |  |
|  |  | B-7 |  |  |  |  |  |  | 200 |
|  | Inorganic particles (C) | C-1 | 400 |  | 200 | 200 |  |  | 200 |
|  |  | C-2 |  |  |  |  |  |  |  |
|  |  | C-3 |  |  |  |  |  |  |  |
|  |  | C-4 |  |  |  |  | 200 |  |  |
|  | Inorganic ultrafine particles (D) | D-1 |  |  |  |  |  |  |  |
|  |  | D-2 |  |  |  |  |  | 100 |  |
| Weight of (B)/Weight of (C) |  |  | 0 | — | 1 | 1 | 1 | — | 1 |
| Handling properties |  |  | 1 | 3 | 2 | 2 | 4 | 1 | 3 |
| Compressive strength (MPa) |  |  | 402 | 350 | 380 | 391 | 421 | 361 | 353 |
| Flexural strength (MPa) |  |  | 136 | 111 | 116 | 138 | 145 | 102 | 112 |
| Polishability (%) |  |  | 74 | 78 | 72 | 81 | 42 | 73 | 79 |

These results show the following. In each of the dental compositions of Examples, the polymerizable monomer (A), the filler (B) having an average particle size of 1 to 20 μm, and the inorganic particles (C) having an average particle size of 0.1 to 1.0 μm are used in combination. The filler (B) includes silica-based fine particles and coatings of an oxide that cover the surfaces of the silica-based fine particles, and the oxide contains at least a zirconium atom, a silicon atom, and an oxygen atom. These dental compositions of Examples each have excellent mechanical strength and polishability as well as excellent handling properties, compared with the dental compositions of Comparative Examples.

More specifically, the dental composition of Comparative Example 1 composed of the polymerizable monomer (A) and the inorganic particles (C) but containing no filler (B) has very poor handling properties. The dental composition of Comparative Example 2 composed of the polymerizable monomer (A) and the filler (B) but containing no inorganic particles (C) has insufficient mechanical strength, compared with the dental compositions of Examples 1 to 28. Similarly, the dental composition of Comparative Example 6 composed of the polymerizable monomer (A), the filler (B), and the inorganic ultafine particles (D) but containing no inorganic particles (C) not only has insufficient mechanical strength but also has very poor handling properties. The dental compositions of Comparative Examples 3 and 4, each in which the average particle size of the filler (B) is beyond the range specified in the present invention, do not provide good handling properties. The dental composition of Comparative Example 5, in which the average particle size of the inorganic particles (C) is beyond the range specified in the present invention (the particles are too large), loses its polishability. Comparative Example 7 shows that the use of the filler (B) having no specified structure reduces the mechanical strength.

It is seen from the comparison between Examples 1 and 2 that the composition using a calcined powder as the filler (B) has higher mechanical strength. Furthermore, it is seen from the comparison among Examples 2, 3, and 4 that the composition containing a calcined powder of the filler (B) having a larger average particle size has higher mechanical strength, and on the other hand, the composition containing a calcined powder having a smaller average particle size has higher polishability.

These results suggest that the dental composition of the present invention has excellent mechanical strength, surface smoothness and gloss after polishing, and gloss durability as a cured product, as well as excellent handling properties as a paste.

INDUSTRIAL APPLICABILITY

The dental composition of the present invention can be used suitably as a substitute for a part of a natural tooth or an entire natural tooth in the field of dental treatment.

The invention claimed is:

1. A dental composition comprising:
   a polymerizable monomer (A);
   50 to 400 parts by weight of an amorphous filler (B) per 100 parts by weight of the polymerizable monomer (A) having an average particle size of 1 to 20 μm and comprising silica-based fine particles and coatings of an oxide that cover the surfaces of the silica-based fine particles, the oxide containing a zirconium atom, a silicon atom, and an oxygen atom; and
   100 to 400 parts by weight of inorganic particles (C) having an average particle size of 0.1 to 1.0 μm per 100 parts by weight of the polymerizable monomer(A),
   wherein the oxide coating covers a plurality of the silica-based fine particles, and
   filler (B) has a structure in which the oxide coating of the silica-based fine particle and the oxide coating of a neighboring silica-based fine particle extend and are connected to each other.

2. The dental composition according to claim 1, wherein the dental composition comprises 100 to 300 parts by weight of the filler (B) and 150 to 300 parts by weight of the inorganic particles (C) per 100 parts by weight of the polymerizable monomer (A).

3. The dental composition according to claim 1, wherein the dental composition comprises 200 to 600 parts by weight of the filler (B) and the inorganic particles (C) in total per 100 parts by weight of the polymerizable monomer (A).

4. The dental composition according to claim 1, wherein the dental composition comprises the filler (B) and the inorganic particles (C) at a weight ratio (the weight of the filler (B)/the weight of the inorganic particles (C)) of 0.2 to 4.0.

5. The dental composition according to claim 1, further comprising inorganic ultrafine particles (D) having an average particle size of 5 to 50 nm.

6. The dental composition according to claim 5, wherein the dental composition comprises 10 to 50 parts by weight of the inorganic ultrafine particles (D) per 100 parts by weight of the polymerizable monomer (A).

7. The dental composition according to claim 1, wherein the inorganic particles (C) comprise silica as a main component.

8. The dental composition according to claim 1, wherein the silica-based fine particles have an average particle size of 2 to 300 nm.

9. The dental composition according to claim 1, wherein in the filler (B), the oxide coating covers each of the silica-based fine particles.

10. The dental composition according to claim 1, wherein filler (B) has a structure in which the oxide coating of the silica-based fine particle and the oxide coating of a plurality of neighboring silica-based fine particles extend and are connected to each other.

11. The dental composition according to claim 1, wherein the filler (B) has a porous particle structure in which the oxide coatings are connected to each other to form an aggregate of the silica-based fine particles covered with the oxide coatings.

12. The dental composition according to claim 1, wherein the filler (B) is a calcined product.

13. The dental composition according to claim 1, wherein the filler (B) further comprises, on the oxide coating, a surface-treated layer of at least one organic metal compound selected from the group consisting of an organic silicon compound, an organic titanium compound, an organic zirconium compound, and an organic aluminum compound.

14. A composite resin comprising the dental composition according to claim 1.

15. The dental composition according to claim 10, wherein the filler (B) has a porous particle structure in which the oxide coating are connected to each other to form an aggregate of the silica-based fine particles covered with the oxide coatings.

16. The dental composition according to claim 10, wherein the filler (B) has a tetrapod or a star structure.

17. The dental composition according to claim 15, wherein in the filler (B) the oxide coating covers each of the silica-based fine particles.

18. The dental composition according to claim 1, wherein polymerizable monomer component (A) comprises a (meth) acrylic acid ester-bade polymerizable monomer.

19. The dental composition according to claim 10, wherein polymerizable monomer component (A) comprises a (meth) acrylic acid ester-bade polymerizable monomer.

* * * * *